United States Patent [19]
Blumbergs et al.

[11] 3,948,985
[45] Apr. 6, 1976

[54] METHOD OF PRODUCING CARBOXYMETHYLOXYSUCCINIC ACID

[75] Inventors: John H. Blumbergs, Highland Park; Michael J. McCarthy, Fanwood; Joseph H. Finley, Metuchen; John M. Polkowski, South River, all of N.J.

[73] Assignee: FMC Corporation, Princeton, N.J.

[22] Filed: Oct. 11, 1974

[21] Appl. No.: 514,018

Related U.S. Application Data

[63] Continuation-in-part of Ser. No. 306,728, Nov. 15, 1972, abandoned.

[52] U.S. Cl. .............................................. 260/535 P
[51] Int. Cl.² ......................................... C07C 59/23
[58] Field of Search ................................ 260/535 P

[56] References Cited
UNITED STATES PATENTS

| | | |
|---|---|---|
| 3,586,715 | 6/1971 | Smeets ........................... 260/535 P |
| 3,821,296 | 6/1974 | Blumbergs et al. ............... 260/535 P |
| 3,824,279 | 7/1974 | Lamberti ........................ 260/535 P |
| R28,192 | 10/1974 | Schulz ........................... 260/535 P |

Primary Examiner—Lorraine A. Weinberger
Assistant Examiner—P. J. Killos

[57] ABSTRACT

Carboxymethyloxysuccinic acid is prepared by acidifying the calcium salt of carboxymethyloxysuccinic acid with sulfuric acid at a temperature of 40°C to 80°C; filtering off the $CaSO_4.2H_2O$ by-product and concentrating the filtrate to give the purified acid. The calcium salt of carboxymethoxysuccinic acid is formed by reacting maleic acid and glycolic acid in aqueous media containing excess calcium hydroxide.

6 Claims, No Drawings

METHOD OF PRODUCING CARBOXYMETHYLOXYSUCCINIC ACID

CROSS-REFERENCE TO RELATED APPLICATIONS

This application is a continuation-in-part of application Ser. No. 306,728, filed Nov. 15, 1972 now abandoned.

This invention relates to an improvement in the production of carboxymethyloxysuccinic acid from maleic and glycolic acid.

Carboxymethyloxysuccinic acid and its alkali metal and quaternary ammonium salts are known chemical entities having utility as biodegradable detergent builders. Detergent compositions containing them are described at length in U.S. Pat. No. 3,635,830.

The preparation of carboxymethyloxysuccinic acid is disclosed in South African Patent application No. 70-7910 of May 24, 1971. According to the procedure therein, maleic acid is reacted with glycolic acid under basic conditions in the presence of zinc or calcium ions. An excess of calcium hydroxide (lime) provides the requisite reaction media. The Michael type addition can be depicted by the following scheme

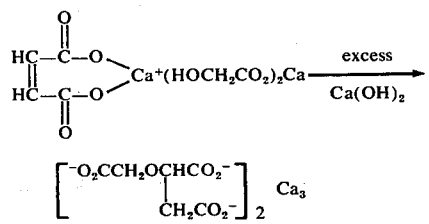

The reaction mixture is treated with aqueous soda ash which precipitates calcium carbonate while forming a solution of the sodium salt of carboxymethyloxysuccinic acid. After removal of the calcium carbonate, the filtrate is evaporated and the carboxymethyloxysuccinic acid recovered as the solid sodium salt. Alternately, the reaction mixture can be contacted with an ion exchange resin which converts the calcium salt of carboxymethyloxysuccinic acid to the free acid form which is isolated by evaporation. The free acid can be neutralized to give the desired alkali or quaternary ammonium salt.

The prior process of producing carboxymethyloxysuccinic acid is satisfactory when working with limited quantities of reactants such as are employed in laboratory preparations or in small pilot installations. From a commercial standpoint, however, this method of obtaining carboxymethyloxysuccinic acid is economically objectionable mainly because of the large amounts of resins required. Aside from initial costs, the use of ion exchange resins for industrial purposes calls for a considerable outlay in plant equipment such as extensive conveying systems, high capacity storage tanks for washing and regeneration and the like.

Moreover, the carboxymethyloxysuccinic acid obtained by treating the reaction mixture with ion exchange resins is impure and contains some unreacted glycolic and maleic acids as well as fumaric acid formed during the reaction. These impurieites are difficult to remove from the crude carboxymethyloxysuccinic acid and their presence is deleterious in detergent compositions in that they have no builder properties thereby diluting rather than enhancing the cleansing action of the detergent agent. Also these impurities are reactive with the chlorine and/or peroxygen bleaches thereby impairing the bleaching ability of the detergent.

A technique that obviates the need for ion-exchange resins and their aforedescribed drawbacks in producing carboxymethyloxysuccinic acid is to acidify the alkaline calcium salt reaction mixture with strong acid after the procedure set forth in U.S. Pat. No. 3,128,287 to Berg for isolating the related 2,2'-oxodisuccinic acid. Thus, Berg prepares 2,2'-oxodisuccinic acid by reacting maleic acid with calcium hydroxide followed by acidification with chilled dilute sulfuric acid. The precipitate of calcium sulfate is removed and the aqueous solution evaporated to give the solid 2,2'-oxodisuccinic acid. Unfortunately, the product is contaminated with calcium sulfate which is very difficult to remove. In fact, Berg obtained the pure acid only after a lengthy and tedious extraction of the crude material with acetic acid in a Soxlet extractor. Such calcium sulfate adulteration is likewise encountered when applying the Berg acidification to the isolation of carboxymethyloxysuccinic acid. Thus, neither the use of ion-exchange resins or the Berg procedure provide a satisfactory process for the manufacture of pure carboxymethyloxysuccinic acid.

It has now been discovered that carboxymethyloxysuccinic acid can be obtained in a practicable and economical manner by a process comprising (a) forming the calcium salt of carboxymethyloxysuccinic acid by reacting maleic acid and glycolic acid in aqueous basic media in the presence of calcium ions; (b) separating the calcium carboxymethyloxysuccinate solids from the reaction mixture; (c) acidifying the resultant calcium salt of carboxymethyloxysuccinic acid with sulfuric acid in the temperature range of 40°C to 80°C thereby producing the free carboxymethyloxysuccinic acid and a precipitate of calcium sulfate dihydrate; (d) removing the calcium sulfate dihydrate; and (e) recovering high purity carboxymethyloxysuccinic acid from its aqueous solution.

The essential feature of the present invention stems from the discovery of the critical temperature range for carrying out the acidification of the calcium salt reaction mixture. At below about 40°C, carboxymethyloxysuccinic acid forms a chelate complex with calcium sulfate, having appreciable solubility in aqueous media. This type of product results where neutralization of the calcium salt is effected with chilling, as specified in the previously cited Berg patent. This results in calcium sulfate appearing in the isolated carboxymethyloxysuccinic acid. On the other hand, if the temperature of the neutralization exceeds about 80°C, calcium sulfate dihydrate undergoes partial dehydration giving rise to lower hydrates, mainly $CaSO_4 \cdot \frac{1}{2}H_2O$ which has a higher water solubility than the dihydrate. Again, the result is contamination of the carboxymethyloxysuccinic acid with calcium sulfate. Preferably, the temperature range is held in the neighborhood of 60°C to 65°C for optimum formation of the insoluble calcium sulfate dihydrate.

In carrying out the process of the invention, an aqueous slurry of the calcium salt of carboxymethyloxysuccinic acid is first prepared. This is conveniently effected in the known manner by the Michael type condensation of maleic acid and glycolic acid in aqueous basic media in the presence of calcium ions. Calcium hydroxide can be used in the double capacity of a base and source of calcium ions. The calcium salt is separated from the reaction mixture by centrifugation or filtration or other known separating means and aqueous slurry of the calcium carboxymethyloxysuccinate is then acidified with sulfuric acid. Formation of the coarse, rapid settling $CaSO_4 \cdot 2H_2O$ is promoted by adding a small quantity of seed crystals prior to acidification. The inorganic precipitate is readily separated, preferably by filtration or centrifugation from the reaction mixture. The resulting solution of carboxymethyloxysuccinic acid is subjected to evaporation leaving a residue of a pure acid. This can be used as such or converted to the desired alkali or ammonium salt for incorporation in detergent compositions.

On a large scale or in commercial production, the process is desirably conducted as a continuous operation in which mother liquors are recycled for recovery or utilization of unreacted starting materials.

were determined by polarographic analyses. The results are summarized in Table I below.

TABLE I

| Reaction Time Min. | pH | Maleic Acid % | Fumaric Acid % | % Conversion |
|---|---|---|---|---|
| 0 | 11.40 | 14.03 | 0 | 0 |
| 15 | 11.52 | 5.29 | <0.05 | 61.9 |
| 30 | 11.60 | 3.17 | 0.077 | 76.9 |
| 45 | 11.74 | 2.11 | 0.13 | 84.0 |
| 60 | 12.04 | 1.27 | 0.26 | 89.1 |
| 75 | 12.10 | 0.90 | 0.29 | 91.5 |
| 90 | 12.10 | 0.54 | 0.34 | 93.7 |
| 105 | 12.13 | 0.52 | 0.34 | 93.9 |
| 120 | 12.11 | 0.40 | 0.35 | 94.7 |

After 2 hours, the reaction mixture was cooled to 65°C and the calcium salt of carboxymethyloxysuccinic acid was separated by centrifugation and the mother liquors were recycled for use in the next batch preparation. A total of five recycle runs were made. The results are listed in Table II below.

TABLE II

PREPARATION OF Ca—CMOS[3]— SEPARATION OF Ca—CMOS AND RECYCLE OF MOTHER LIQUOR

| Starting Materials, g | Run 48 | Run 49 | Run 53 | Run 54 | Run 57 | Run 67 |
|---|---|---|---|---|---|---|
| Maleic anhydride | 200 | 200 | 200 | 200 | 200 | 200 |
| Glycolic acid (70%) | 244 | 225 | 225 | 225 | 225 | |
| Ca(OH)$_2$ | 258 | 255 | 255 | 255 | 255 | 250[1] |
| H$_2$O | 1000 | 400 | — | — | 100 | 191 |
| Recycle mother liquor | — | 870 | 1077 | 1038 | 992 | 913 |
| (from Run No.) | | (48) | (49) | (53) | (54) | (58) |
| Initial pH, measured at 25°C | 11.6 | 11.6 | 11.35 | 11.45 | 11.25 | 11.32 |
| % Conversion | | | | | | |
| 15 min. | | | | | | 76.1 |
| 30 min. | | | | | 82.8 | 84.8 |
| 45 min. | | | | | | 95.5 |
| 60 min. | 84.0 | 76.1 | 90.7 | 91.6 | 90.0 | 94.4 |
| 90 min. | | | | | 93.4 | |
| 120 min. | 93.7 | 92.7 | 91.6 | 92.5 | 93.3 | |
| 150 min. | | | | | 93.0 | |
| Product Obtained | | | | | | |
| Wet Ca—CMOS, g | 510 | 541 | 562 | 520 | 509 | 544 |
| % Moisture in cake | 26.7 | 19.2 | 15.0 | 9.6 | 13.8 | 17.6 |
| % Ca-Maleate and fumarate in dry cake | 3.1 | 3.9 | 3.8 | 3.9 | 4.3 | 1.2 F.A.[2] 1.0 M.A. |
| Mother liquor, g | 1057 | 1312 | 1054 | 1012 | 925 | 1099 |
| % Maleic and fumaric in mother liquor | 0.25 | 0.1 | 0.1 | 0.1 | 0.1 | 0.15 |

[1]Fresh Ca(OH)$_2$ used
[2]Analyzed for glycolic acid and found less than 0.1%
[3]Calcium salt of carboxymethyloxysuccinic acid Reference is made to the following non-limiting examples.

EXAMPLE 1

Into a 1000 ml beaker was charged 200 g of maleic anhydride (2.04 mole) and 500 ml of distilled water and the mixture stirred at room temperature until all maleic anhydride was dissolved (approximately 30–40 minutes). Into a 3-liter, round bottom jacketed flask, supplied with a laboratory stirrer, condenser and thermometer, was charged 257 g of Ca(OH)$_2$ (Fisher C.P. grade) and 500 ml of water. To the maleic acid solution was added 231 g of 68.5% glycolic acid (2.08 mole) and the acid mixture was charged into the reaction flask with good stirring. The temperature rose to 95°C. Low pressure steam was applied in the jacket to maintain a temperature in the reaction flask at 100°–102°C. Samples of the reaction mixture were withdrawn every 15 minutes and were analyzed for pH, maleic and fumaric acid contents. The pH measurement was done at room temperature. The maleic and fumaric acids The maleic anhydride was dissolved in a portion of the mother liquor (usually in 400–500 ml). The remainder of the mother liquor was charged into the reaction flask containing the desired amount of lime. The glycolic acid was mixed with the maleic acid solution and was then added to the lime slurry in flask.

As seen in Table II, high yields of calcium salt of carboxymethyloxysuccinic acid were obtained and no deleterious effect was observed on the yields or product quality by recycling the mother liquors. Practically all of the unreacted calcium glycolate remained in the mother liquors, but some of the calcium maleate and fumarate remained in the cake of the calcium salt of carboxymethyloxysuccinic acid. The wet cakes of the calcium salt of carboxymethyloxysuccinic acid from all mixtures were combined and the composite sample was analyzed. Found: 15.1% moisture, 3.1% double bond, calculated as calcium maleate and fumarate and less than 0.1% calcium glycolate.

Five hundred grams of the composite wet cake as above described was mixed with 1000 ml of water with good stirring, heated to 60°C and timed for an additional 30 minutes. To this slurry was added 10 g of $CaSO_4 \cdot 2H_2O$ crystals. Then 265 g of conc. sulfuric acid were slowly added with good stirring, maintaining the temperature of the slurry at 60°–65°C. Sulfuric acid addition time was 20 minutes. The slurry was stirred at 60°C for an additional 30 minutes and was then cooled to 18°C. Then it was centrifuged and the $CaSO_4 \cdot 2H_2O$ crystals, formed by sulfuric acid reaction with calcium carboxymethyloxysuccinic acid was washed with 200 ml of distilled water in the centrifuge. The filtrate contained high purity carboxymethyloxysuccinic acid. Analyses showed that this carboxymethyloxysuccinic acid solution contains less than 0.02% glycolic acid, 120 ppm of Ca, 0.06% maleic acid and 0.41% fumaric acid indicating 97+% purity on solid bases.

Part of the carboxymethyloxysuccinc acid solution was neutralized with 50% NaOH solution to pH=9.0 and was then flash dried under reduced pressure to give the trisodium salt in high purity.

EXAMPLE 2

The same procedure described in Example 1 was used for pilot production of calcium carboxymethyloxysuccinate. Synthesis were carried out in a 300 gallon stainless steel reactor equipped with two blade type stirrers and a heating jacket. The vessel was charged with approximately 190 gallons of mother liquor from a previous run and 220 pounds of maleic anhydride was added. After all maleic anhydride was dissolved, 218 pounds of 70% glycolic acid and 300 pounds of lime was added with sufficient stirring. The reaction mixture was heated to 100°–102°C for two hours and the calcium carboxymethyloxysuccinate product was separated by centrifugation. Usually the starting pH of the reaction mixture after adding the lime was in the range of 11.3 to 11.5 measured at room temperature and the calcium carboxymethyloxysuccinate product contained 2–3 percent total of calcium fumarate and maleate and only 0.1% to 0.5% of calcium glycolate. The product quality was acceptable for further work-up to produce trisodium carboxymethyloxysuccinate.

Due to a slight overcharge of lime the starting pH of the reaction mixture was 12.0 and after two hours reaction time and separation of the product, analyses showed the presence of large amounts of calcium fumarate and this product was not suitable for further work-up.

The product was dried and was analyzed. Found: 14.2% total of calcium fumarate and maleate with ratio of fumarate to maleate of 96:4, indicating that the product from this run contained 13.6% by weight of calcium fumarate and 0.6% of calcium maleate. This contaminated calcium carboxymethyloxysuccinate product was used as starting material for laboratory purification study.

Two hundred grams of the crude product was charged in a beaker and 362 ml of distilled water was added. The mixture was heated to 60°–80°C and maintained for one hour with good stirring. Then 123 grams of 96.5% sulfuric acid was slowly added maintaining the temperature at 60°C for one hour. The slurry was then cooled in an ice-water bath and aliquots were taken at various temperatures. These were filtered and the filtrates were analyzed for $Ca^{++}$ content by atomic absorption and for maleic and fumaric acid content by the polargraphic method. The results are listed in Table III.

TABLE III

| Temperature °C | $Ca^{++}$ Content ppm | Maleic Acid Content | Fumaric Acid Content |
|---|---|---|---|
| 60 | 339 | 0.14 | 1.67 |
| 40 | 263 | 0.06 | 0.84 |
| 30 | 209 | 0.08 | 0.56 |
| 20 | 162 | 0.05 | 0.41 |
| 10 | 131 | 0.05 | 0.29 |

In this experiment a stoichiometric amount of concentrated sulfuric acid was used, based on the calcium content.

This experiment was repeated by using 129 grams of concentrated sulfuric acid, which is a slight excess of stoichiometric amount. The results are listed in Table IV.

TABLE IV

| Temperature °C | $Ca^{++}$ Content ppm | Maleic Acid Content | Fumaric Acid Content |
|---|---|---|---|
| 60 | 265 | 0.11 | 1.67 |
| 40 | 188 | 0.06 | 0.72 |
| 30 | 215 | 0.05 | 0.56 |
| 20 | 164 | 0.06 | 0.37 |
| 10 | 142 | 0.06 | 0.27 |

These experiments clearly demonstrate that by the procedure of this invention pure carboxymethyloxysuccinic acid can be clearly obtained from crude calcium carboxymethyloxysuccinate containing high concentrations of unwanted impurities. The filtrates from both experiments obtained by removal of the calcium sulfate solids at 10°C give carboxymethyloxysuccinic acid of 97%+ purity. The principal impurity — fumaric acid can be recovered from the calcium sulfate dihydrate solids by conventional methods of extraction with organic solvents.

What is claimed is:

1. In the process of producing carboxymethyloxysuccinic acid including the steps (a) forming the calcium salt of carboxymethyloxysuccinic acid by reacting maleic acid and glycolic acid in aqueous basic media in the presence of calcium ions; (b) acidifying the resultant calcium salt of carboxymethyloxysuccinic acid with sulfuric acid calcium sulfate; (c) removing the calcium sulfate; and (d) recovering carboxymethyloxysuccinic acid from its aqueous solution, the improvement which comprises carrying out the acidification between about 40°C and 80°C whereby the calcium sulfate precipitates as the dihydrate.

2. The process according to claim 1 where the acidification is carried out between about 60°C to about 65°C.

3. The process according to claim 1 wherein the calcium hydroxide provides the basic media and source of calcium ions.

4. The process according to claim 1 wherein the carboxymethyloxysuccinic acid is recovered by evaporation from its aqueous solution.

5. The process according to claim 1 wherein the calcium salt prior to acidification is separated from the reaction mixture.

6. The process according to claim 1 carried out continuously.

* * * * *

UNITED STATES PATENT OFFICE
CERTIFICATE OF CORRECTION

PATENT NO. : 3,948,985
DATED : April 6, 1976
INVENTOR(S) : John H. Blumbergs, et al It is certified that error appears in the above-identified patent and that said Letters Patent are hereby corrected as shown below:

Patent Abstract, line 6, "carboxymethoxysuccinic" should read --carboxymethyloxysuccinic--.

Patent Table II, under column heading "Run 67", line "Glycolic acid (70%)" should be inserted --225--.

Column 6, line 48, between "acid" and "calcium" should be inserted --thereby producing the free carboxymethyloxysuccinic acid and--.

Signed and Sealed this

Fourteenth Day of December 1976

[SEAL]

Attest:

RUTH C. MASON
Attesting Officer

C. MARSHALL DANN
Commissioner of Patents and Trademarks